United States Patent
Olson et al.

(10) Patent No.: US 6,540,743 B2
(45) Date of Patent: *Apr. 1, 2003

(54) RESILIENT RADIOPAQUE ELECTROPHYSIOLOGY ELECTRODES AND PROBES INCLUDING THE SAME

(75) Inventors: Steven L. Olson, Sunnyvale, CA (US); Sidney D. Fleischman, Menlo Park, CA (US); David K. Swanson, Mountain View, CA (US); Russell B. Thompson, Los Altos, CA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/826,200

(22) Filed: Apr. 3, 2001

(65) Prior Publication Data

US 2001/0014770 A1 Aug. 16, 2001

Related U.S. Application Data

(63) Continuation of application No. 09/378,360, filed on Aug. 20, 1999, now Pat. No. 6,245,068, which is a continuation-in-part of application No. 09/055,175, filed on Apr. 3, 1998, now Pat. No. 6,030,382, which is a continuation-in-part of application No. 08/558,131, filed on Nov. 13, 1995, now Pat. No. 5,797,905, and a continuation-in-part of application No. 08/439,282, filed on May 12, 1995, now abandoned, which is a continuation-in-part of application No. 08/287,192, filed on Aug. 8, 1994, now abandoned.

(51) Int. Cl.[7] .................................................. A61B 18/18
(52) U.S. Cl. ........................................ 606/41; 600/374
(58) Field of Search ................ 606/40–42, 45, 606/46, 48–50; 607/101, 102; 600/374

(56) References Cited

U.S. PATENT DOCUMENTS

| | | | |
|---|---|---|---|
| 4,172,451 A | * | 10/1979 | Kline ........................ 600/374 |
| 4,522,212 A | | 6/1985 | Gelinas et al. |
| 4,671,291 A | | 6/1987 | Wilson |
| 4,966,597 A | | 10/1990 | Cosman |
| 5,057,105 A | | 10/1991 | Malone et al. |
| 5,122,137 A | | 6/1992 | Lennox |
| 5,178,620 A | | 1/1993 | Eggers et al. |
| 5,334,193 A | | 8/1994 | Nardella |
| 5,345,936 A | | 9/1994 | Pomeranz et al. |
| 5,360,432 A | | 11/1994 | Shturman |
| 5,364,352 A | * | 11/1994 | Cimino et al. .............. 604/264 |
| 5,400,789 A | | 3/1995 | Griffith |
| 5,406,946 A | | 4/1995 | Imran |
| 5,409,000 A | | 4/1995 | Imran |
| 5,411,025 A | * | 5/1995 | Webster, Jr. ................ 600/374 |
| 5,423,811 A | | 6/1995 | Imran et al. |
| 5,437,290 A | | 8/1995 | Bolger et al. |
| 5,443,463 A | | 8/1995 | Stern et al. |
| 5,456,682 A | | 10/1995 | Edwards et al. |
| 5,478,330 A | * | 12/1995 | Imran et al. ................ 604/525 |
| 5,509,411 A | | 4/1996 | Littmann et al. |
| 5,582,609 A | * | 12/1996 | Swanson et al. ............. 606/33 |
| 5,606,981 A | | 3/1997 | Tartacower et al. |
| 5,628,771 A | | 5/1997 | Mizukawa |
| 5,673,695 A | | 10/1997 | McGee et al. |
| 5,797,905 A | | 8/1998 | Fleischman et al. |
| 5,810,802 A | | 9/1998 | Panescu et al. |
| 5,824,077 A | | 10/1998 | Mayer |
| 6,030,382 A | | 2/2000 | Fleischman et al. |
| 6,048,329 A | * | 4/2000 | Thompson et al. ......... 600/374 |
| 6,063,082 A | * | 5/2000 | DeVore et al. .............. 606/170 |
| 6,245,068 B1 | | 6/2001 | Olson et al. |

* cited by examiner

Primary Examiner—Michael Peffley
(74) Attorney, Agent, or Firm—Henricks, Slavin & Holmes LLP

(57) ABSTRACT

A coil electrode for use in an electrophysiology probe includes a first material having a relatively high radiopacity and a second material having a relatively high resiliency. This combination provides the necessary levels of durability, resiliency and radiopacity. An electrophysiological probe includes a support structure, at least one first electrode defining a first radiopacity supported on the support structure and at least one second electrode defining a second radiopacity supported on the support structure, the second radiopacity being greater than the first radiopacity. When viewed under a fluoroscope, the pattern of electrodes of varying radiopacities allows the physician to distinguish between individual electrodes.

21 Claims, 6 Drawing Sheets

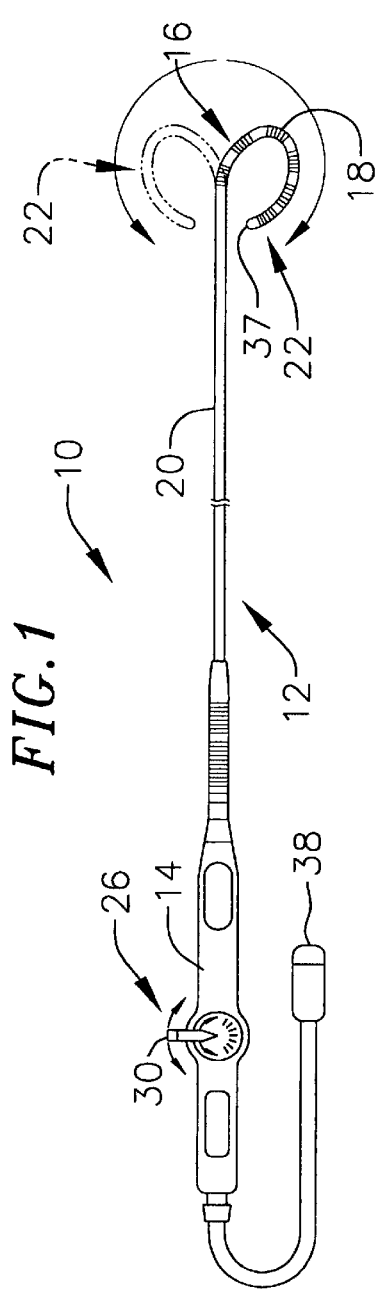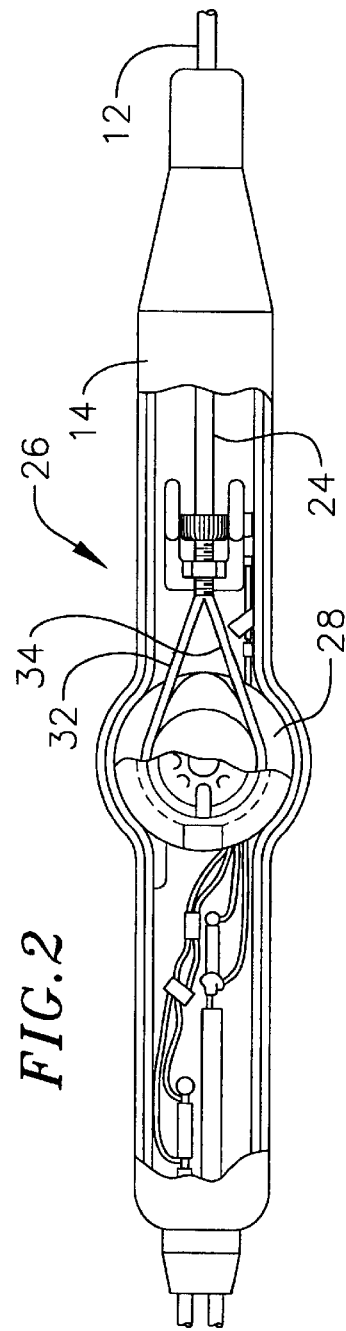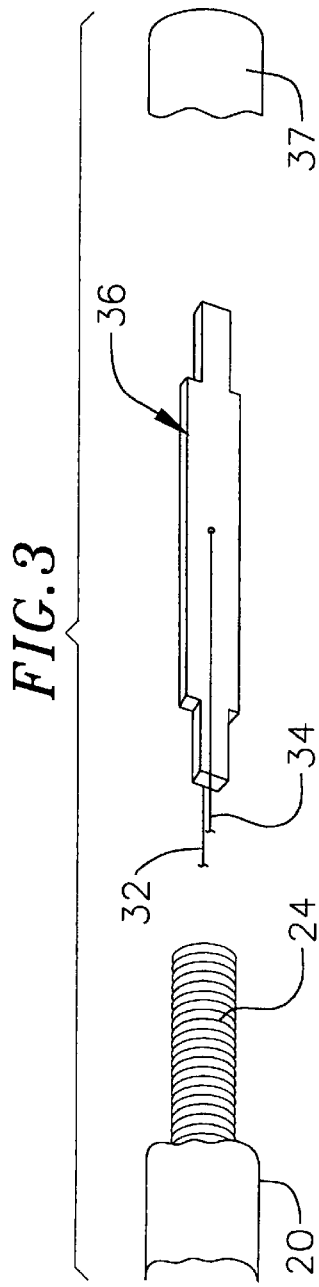

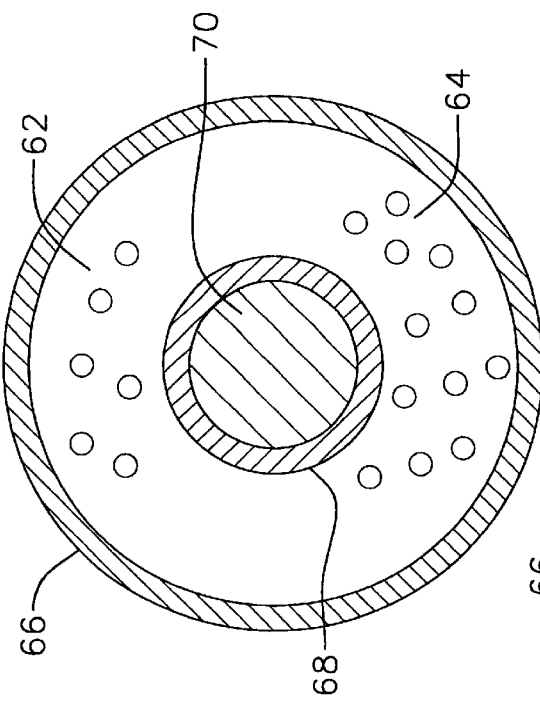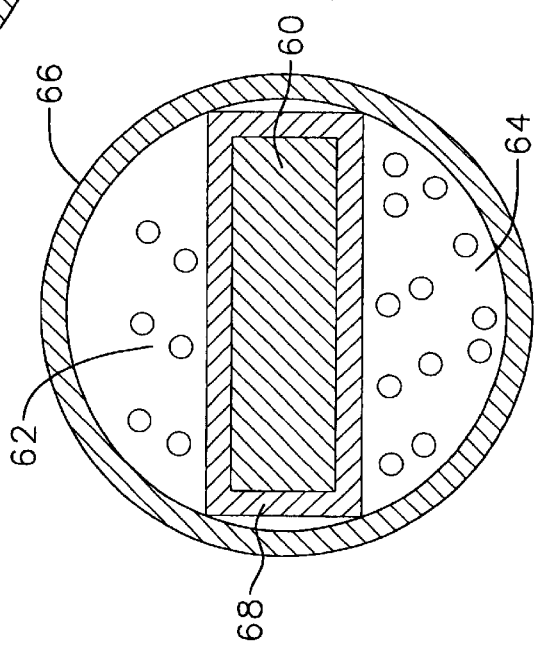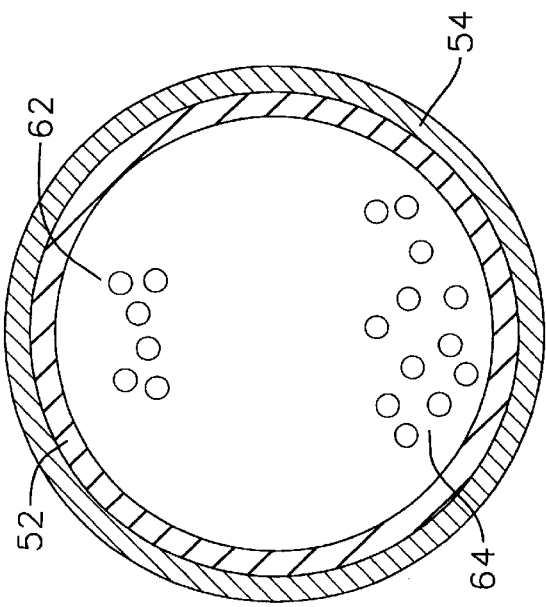

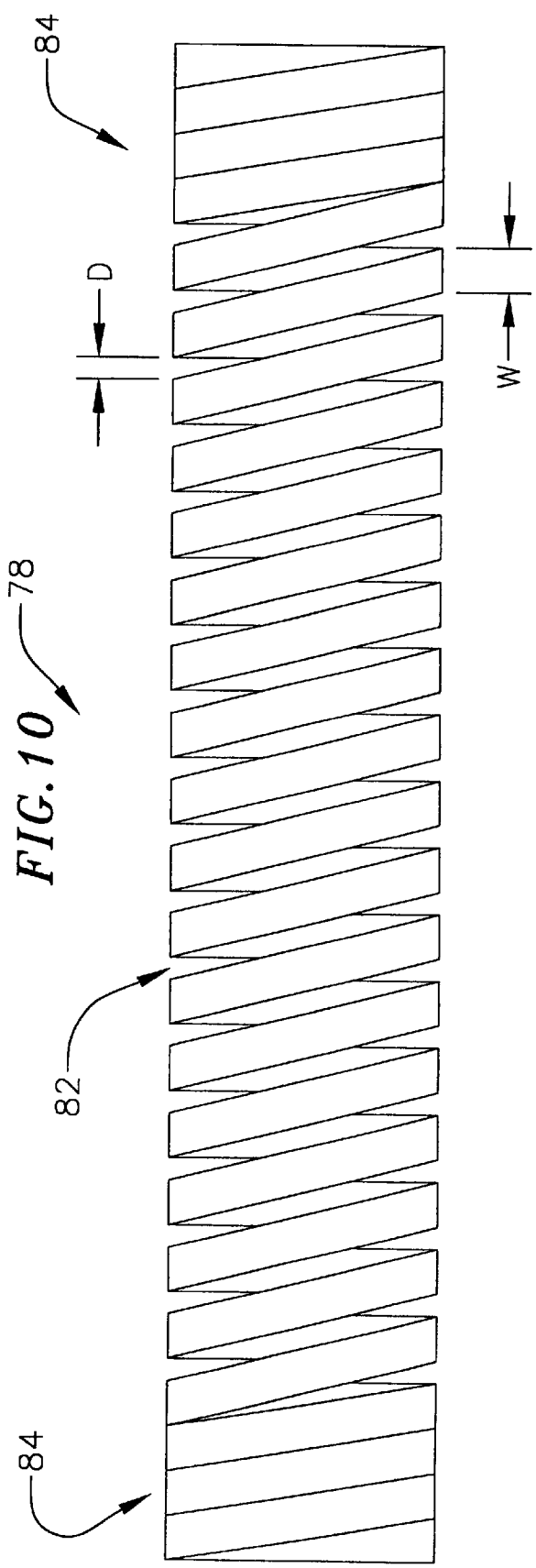
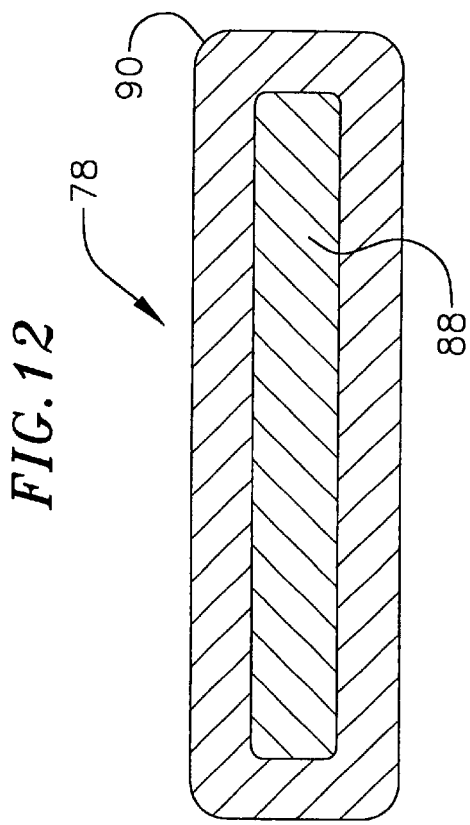
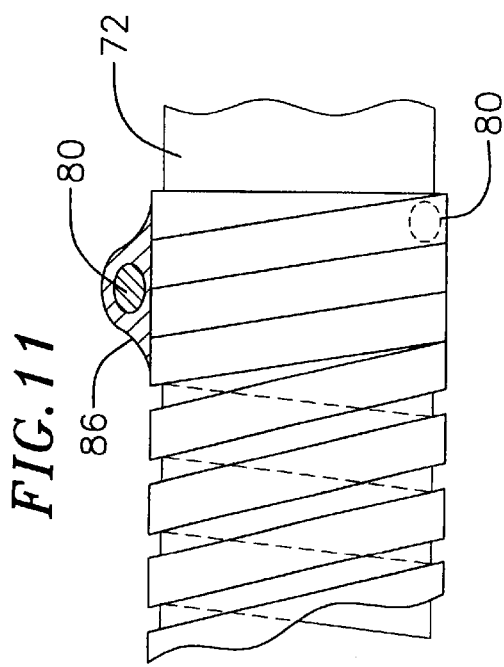
FIG. 10
FIG. 12
FIG. 11

RESILIENT RADIOPAQUE ELECTROPHYSIOLOGY ELECTRODES AND PROBES INCLUDING THE SAME

CROSS-REFERENCE TO RELATED APPLICATIONS

This application is a continuation of U.S. application Ser. No. 09/378,360, filed Aug. 20, 1999, now U.S. Pat. No. 6,245,068, which is itself a continuation-in-part of U.S. application Ser. No. 09/055,175, filed Apr. 3, 1998, now U.S. Pat. No. 6,030,382, which is itself a continuation-in-part of U.S. application Ser. No. 08/558,131, filed Nov. 13, 1995, now U.S. Pat. No. 5,797,905, which is itself a continuation-in-part of both U.S. application Ser. No. 08/287,192, filed Aug. 8, 1994, now abandoned, and U.S. application Ser. No. 08/439,282, filed May 12, 1995, now abandoned, all of which are incorporated herein by reference.

BACKGROUND OF THE INVENTIONS

1. Field of Inventions

The present inventions relate generally to electrophysiology probes such as catheters and surgical probes and, more particularly, to electrodes for use with electrophysiology probes.

2. Description of the Related Art

Catheters, surgical probes and related electrophysiological devices (together referred to herein as "electrophysiological probes" or "probes") are used today in diagnostic and therapeutic medical procedures that require surgical or minimally invasive access to targeted tissue areas within interior regions of the body. The probes include support bodies that typically carry an array of linearly spaced electrodes at the distal end thereof. Probe power control systems that allow physicians to individually control the power applied to the electrodes in such multiple electrode probes are also available. One example of such a system is disclosed in U.S. Pat. No. 5,545,193.

Precise positioning of the electrodes is of paramount importance in all probe-based procedures. However, the need for careful and precise positioning of the electrodes is especially critical during certain procedures concerning the heart. These procedures, called electrophysiological therapy, are becoming more widespread for treating cardiac rhythm disturbances. Cardiac tissue coagulation (sometimes referred to as "ablation"), where therapeutic lesions are formed in cardiac tissue, is one procedure in which the ability to precisely position the electrodes is especially important. During catheter-based procedures, a physician steers the catheter through a main vein or artery into the region of the heart that is to be treated. In surgical probe-based procedures, the distal portion of the probe is inserted through the patient's chest and directly into the heart. The physician must then precisely place the linear array of electrodes near the cardiac tissue that is to be coagulated. Fluoroscopic imaging in often used to identify anatomic landmarks within the heart and to position the electrodes relative to the targeted tissue region. Once the electrodes are properly positioned, the physician directs energy from the electrodes to the tissue to form a lesion.

Rigid ring-shaped electrodes were originally used in electrophysiological probes. In recent years, coil electrodes have been introduced in order to increase the flexibility of the distal portion of the probes, thereby enabling the physician to more precisely control the position and shape of the distal portion of the probe and to achieve superior tissue contact. The metals used to manufacture conventional coil electrodes have been heretofore selected according to certain mechanical properties, the primarily property being resiliency. A relatively high level of resiliency is required during the various manufacturing processes, such as coil winding and the mounting of coils onto a probe, because relatively resilient material returns to its original shape after being manipulated during manufacturing, as compared to softer, less resilient materials such as platinum or gold which can be permanently deformed during manufacturing. Relatively resilient materials are also more durable than softer, less resilient materials. Another desirable mechanical property is stiffness. Accordingly, coil electrodes have been formed from relatively resilient and stiff materials and, more specifically, from stainless steel.

The radiopacity of stainless steel is, however, relatively low. Thus, while otherwise superior to coil electrodes formed from less resilient materials such as platinum or gold, stainless steel coil electrodes are difficult to visualize using fluoroscopic imaging techniques. The low visibility of conventional stainless steel coil electrodes makes it difficult to properly position the distal portion of the probe. It is also difficult to differentiate between individual coil electrodes which, in turn, makes individual control of the electrodes difficult even when the distal portion of the probe is properly positioned. The difficulties associated with electrode differentiation are further compounded when the probe includes a relatively large number of electrodes.

One proposed solution to this problem has been to include radiopaque markers on probes in addition to the electrodes. The inventors herein have determined that this proposed solution is less than optimal because the electrodes must be closely spaced in order to insure reliable creation of contiguous lesions between adjacent electrodes. The close spacing precludes the placement of radiopaque markers between the electrodes.

SUMMARY OF THE INVENTION

The inventors herein have determined that a need exists for an electrophysiology probe having coil electrodes that are both resilient and radiopaque. Accordingly, one object of the present invention is to provide an electrophysiology probe having one or more coil electrodes that have relatively high levels of resiliency and radiopacity. Another object of the present invention is to provide an electrophysiological probe having an electrode arrangement that facilitates electrode identification.

In order to accomplish some of these and other objectives, a coil electrode for use in an electrophysiology probe in accordance with a present invention is formed from a first material having a relatively high radiopacity and a second material having a relatively high resiliency. In one embodiment, the electrode includes a stainless steel cladding over a relatively soft 90/10 platinum/iridium core. The stainless steel cladding provides the necessary levels of durability and resiliency for coil winding and assembly, while the platinum/iridium core provides the necessary level of radiopacity.

In order to accomplish some of these and other objectives, an electrophysiological probe in accordance with a preferred embodiment of a present invention includes a support structure, at least one first electrode defining a first radiopacity supported on the support structure and at least one second electrode defining a second radiopacity supported on the support structure, the second radiopacity being greater than the first radiopacity. In one embodiment, the probe includes a plurality of first and second electrodes arranged in a predetermined pattern. When viewed under a fluoroscope, the pattern of objects having relatively high and low radiopacities allows the physician to distinguish between individual electrodes.

The above described and many other features and attendant advantages of the present inventions will become apparent as the inventions become better understood by reference to the following detailed description when considered in conjunction with the accompanying drawings.

BRIEF DESCRIPTION OF THE DRAWINGS

Detailed description of preferred embodiments of the inventions will be made with reference to the accompanying drawings.

FIG. 1 is a plan view of an electrophysiology probe in accordance with a preferred embodiment of a present invention.

FIG. 2 is a cutaway view of the electrophysiology probe handle illustrated in FIG. 1.

FIG. 3 is an exploded view of certain components of the distal portion of the electrophysiology probe illustrated in FIG. 1.

FIG. 5 is a section view of the proximal portion of the electrophysiological probe shaft illustrated in FIG. 4 taken along line 5—5 in FIG. 4.

FIG. 6 is a section view of the distal portion of the electrophysiological probe illustrated in FIG. 4 taken along line 6—6 in FIG. 4.

FIG. 7 is a section view of a preferred electrophysiological probe distal portion.

FIG. 10 is a side view of an electrode in accordance with another preferred embodiment of a present invention.

FIG. 11 is a partial side view of the electrode illustrated in FIG. 10 mounted on a support structure with a temperature sensor.

FIG. 12 is a section view of the electrode illustrated in FIG. 10.

DETAILED DESCRIPTION OF THE PREFERRED EMBODIMENTS

Figure 4:
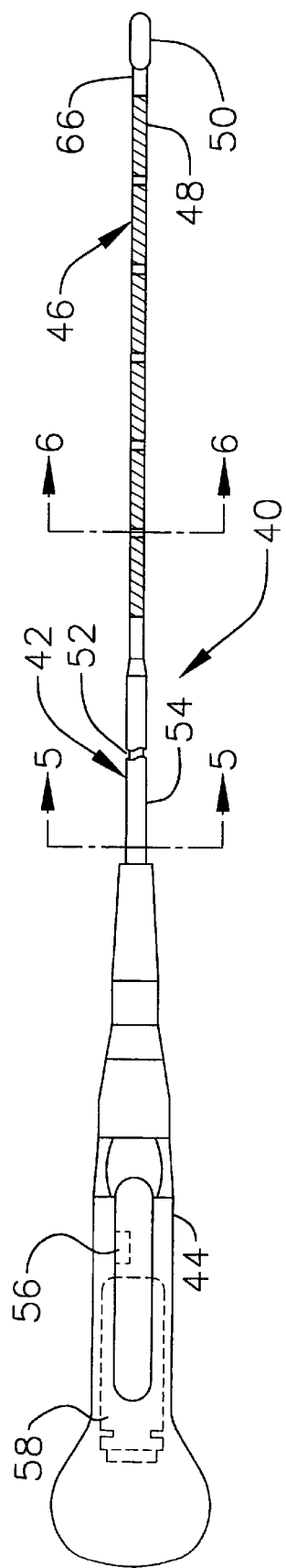
FIG. 4 is a plan view of an electrophysiology probe in accordance with another preferred embodiment of a present invention.

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:
 I. Introduction
 II. Electrophysiological Probe Structures
 III. Electrophysiological Probe Electrodes
 IV. Electrode Identification The section titles and overall organization of the present detailed description are for the purpose of convenience only and are not intended to limit the present inventions.

I. Introduction

The present inventions are directed generally to electrophysiological probes and electrophysiological probe electrodes that may be used within body lumens, chambers or cavities for diagnostic or therapeutic purposes without complex invasive surgical procedures. The inventions herein have particular application in the diagnosis and treatment of arrhythmia conditions within the heart because they can facilitate intimate tissue contact with target substrates associated with various arrhythmias, namely atrial fibrillation, atrial flutter, and ventricular tachycardia. Nevertheless, it should be appreciated that the electrophysiological probes and electrodes are applicable for use in therapies involving other types of soft tissue. For example, various aspects of the present inventions have applications in procedures concerning other regions of the body such as the prostate, liver, brain, gall bladder, uterus and other solid organs.

II. Electrophysiological Probe Structures

As illustrated for example in FIGS. 1–3, an electrophysiological probe in accordance with a preferred embodiment of a present invention may be in the form of a catheter 10 including a catheter body 12 and a handle 14. The distal portion 16 of the catheter body 12 supports a plurality of coil electrodes 18. The catheter body 12 preferably consists of two tubular parts, or members. The proximal member 20 is relatively long and is attached to the handle 14, while the distal member 22, which is relatively short, carries the coil electrodes 18. The proximal member 20 is typically formed from material, such as braided PEBAX® (with a hardness durometer of 55D), which has better torque transmission properties than the distal member 22, which is typically formed from a softer, more flexible material such as PEBAX® (with a hardness durometer of 35D), that is better for steering. A guide coil 24 is disposed within the central lumen of the proximal member 20. Additional details concerning such a catheter body are disclosed in U.S. application Ser. No. 09/150,833, filed Sep. 10, 1998, entitled "Catheter Having Improved Torque Transmission Capabilities and Method of Making the Same," which is incorporated herein by reference.

The exemplary catheter 10 also includes a steering mechanism 26 that may be used to deflect the distal portion 16 of the catheter body 12 in the manner illustrated in FIG. 1. In the preferred embodiment, the steering mechanism 26 consists of a rotatable cam wheel 28 and steering lever 30 arrangement that is mounted on the handle 14 and a pair of steering wires 32 and 34 that are secured to opposite sides of a steering spring 36 (sometimes referred to as a "center support"). One end of the steering spring is secured to the distal end of the guide coil 24 and the other end is secured to a catheter tip 37. Additional details concerning this and other steering arrangements are disclosed in U.S. Pat. No. 5,254,088, which is incorporated herein by reference, as well as in the aforementioned U.S. application Ser. No. 09/150,833.

Figure 9A:
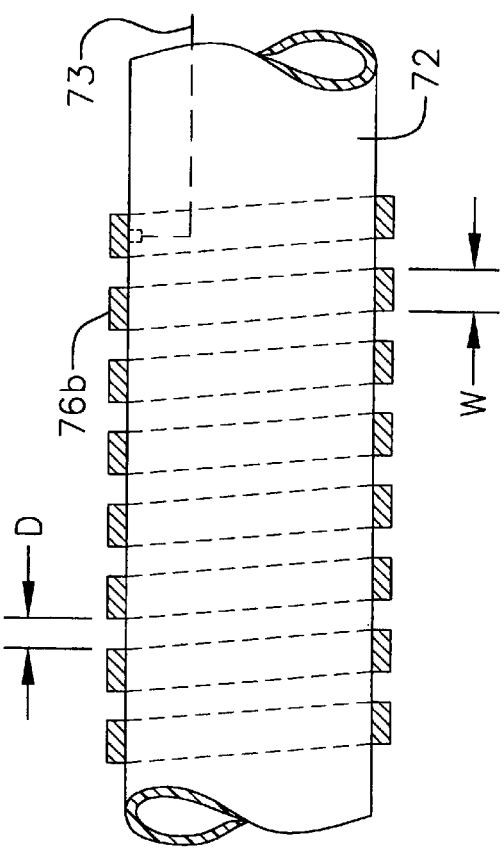
FIG. 9a is a side, partial section view of an electrode and support structure in accordance with still another preferred embodiment of a present invention.
Figure 9B:
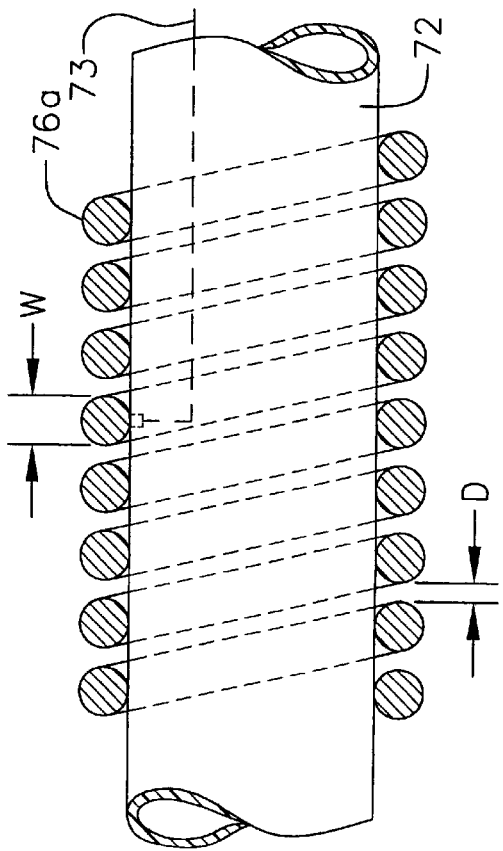
FIG. 9b is a side, partial section view of an electrode and support structure in accordance with yet another preferred embodiment of a present invention.

The exemplary catheter 10 may be used in conjunction with a conventional tissue mapping and coagulation energy supply apparatus wherein power from an electromagnetic radio frequency (about 10 kHz to about 3 GHz) generator is supplied to the electrodes and controlled based upon temperature. To that end, and as discussed in Section III below, a plurality of temperature sensors (such as thermocouples or thermistors) may be located on, under, abutting the longitudinal end edges of, or in between, the electrodes 18. A plurality of lead (or "signal") wires are electrically connected to the electrodes 18 and temperature sensors, extend through the catheter body 12 into the handle 14, where they are electrically coupled to an external connector 38 (note, for example, wire 73 in FIGS. 9a and 9b). The connector 38 connects the electrodes 18 and temperature sensors to the mapping and energy supply apparatus. The apparatus should be operable in both bi-polar and uni-polar modes. When operated in a uni-polar mode, an external patch electrode (not shown) constitutes the radio frequency energy return line.

As shown by way of example in FIGS. 4–7, an electrophysiological probe in accordance with another preferred embodiment of a present invention may be in the form of a surgical probe 40 that includes a relatively short, relatively stiff shaft 42, a handle 44 and a distal section 46. The distal section 46 supports a plurality of coil electrodes 48 and a tip electrode 50. The shaft 42 may be from about 4 inches to 18 inches in length and is preferably about 6 to 8 inches. The distal section 46 may be from about 1 inch to 10 inches in length and is preferably about 4 to 6 inches. This embodiment is particularly useful because it can be easily inserted into the patient through an introducing port such as a trocar.

The exemplary shaft 42 illustrated in FIGS. 4 and 5 consists of a hypo-tube 52, which is relatively stiff, and an outer polymer tubing 54 over the hypo-tube. A "relatively stiff" shaft (or other structural element) is either rigid, malleable, or somewhat flexible. A rigid shaft cannot be bent. A malleable shaft is a shaft that can be readily bent by the physician to a desired shape, without springing back when released, so that it will remain in that shape during the surgical procedure. Thus, the stiffness of a malleable shaft must be low enough to allow the shaft to be bent, but high enough to resist bending when the forces associated with a surgical procedure are applied to the shaft. A somewhat flexible shaft will bend and spring back when released. However, the force required to bend the shaft must be substantial. A malleable or somewhat flexible shaft will preferably have a bending modulus of between approximately 3 lb.-in.$^2$ and approximately 50 lb.-in.$^2$. Rigid and somewhat flexible shafts are preferably formed from stainless steel, while malleable shafts are formed from annealed stainless steel.

The exemplary surgical probe 40 illustrated in FIGS. 4–7 is also intended to be used in conjunction with a conventional tissue mapping and coagulation energy supply apparatus. Here too, a plurality of temperature sensing elements may be located on, under, abutting the longitudinal end edges of, or in between, the electrodes. Additionally, a reference temperature sensor 56 may be provided in the handle 44 so that room temperature will be used as the reference. The handle 44 also includes a PC board 58 for connecting the electrodes and temperature sensors to the power source. The supply of power to the electrodes may be turned on and off with a foot switch. Alternatively, the handle 44 may be provided with a manually operable global on-off switch that can selectively enable and disable the supply of energy to all of the electrodes. The handle 44 may also include a plurality of individual on-off switches for each electrode.

The distal section 46 of the exemplary probe 40 can be either somewhat flexible, in that it will conform to a surface against which it is pressed and then spring back to its original shape when removed from the surface, or malleable. As shown by way of example in FIG. 6, a somewhat flexible distal section 46 may include a spring member 60, which is preferably either a solid flat wire spring (as shown), a round wire, or a three leaf flat wire Nitinol spring, that is connected to the distal end of the hypo-tube 52. Other spring members, formed from materials such as 17–7 or 455 carpenters steel, may also be used. A series of lead wires 62 and 64 connect the electrodes 48 and 50 and temperature sensors, respectively, to the PC board 58. The spring member 60 and lead wires 62 and 64 are enclosed in a flexible body 66, preferably formed from PEBAX® material, polyurethane, or other suitable materials. The spring member 60 may also be pre-stressed so that the distal tip is pre-bent. An insulating sleeve 68 may be placed between the spring member 60 and the lead wires 62 and 64. In those instances where a malleable distal section 46 is desired, the spring member 60 may be replaced by a mandrel 70 made of suitably malleable material such as annealed stainless steel or beryllium copper, as illustrated for example in FIG. 7.

Additional information concerning the above-described and other surgical probes may be found in U.S. application Ser. No. 09/072,872, filed May 5, 1998, entitled "Surgical Method and Apparatus for Positioning a Diagnostic or Therapeutic Element Within the Body," which is incorporated herein by reference.

III. Electrophysiological Probe Electrodes

Figure 8A:
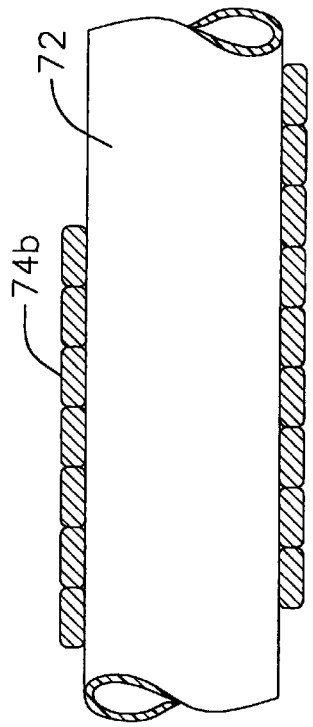
FIG. 8a is a side, partial section view of an electrode and support structure in accordance with a preferred embodiment of a present invention.
Figure 8B:
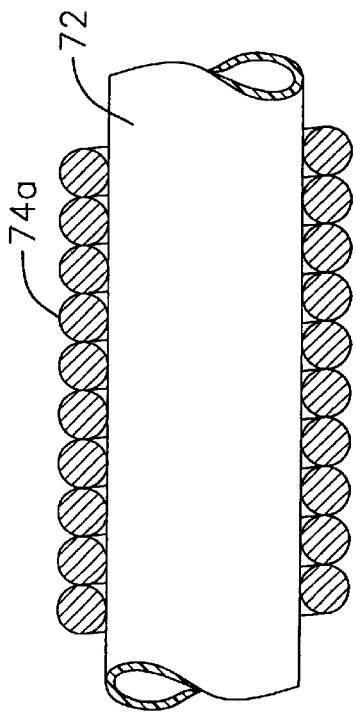
FIG. 8b is a side, partial section view of an electrode and support structure in accordance with another preferred embodiment of a present invention.

As illustrated in FIGS. 8a–12, there are a variety of coil electrode configurations that may be used in conjunction with the electrophysiological probes described above as well as other electrophysiological probes. Referring first to FIG. 8a, an electrophysiological probe support structure 72 (such as the catheter distal section 16 or surgical probe distal section 46) may be used to carry an array of spaced apart, generally flexible coil electrodes 74a. In this embodiment, each of the coil electrodes 74a is relatively tightly wound and is circular in cross-section. Alternatively, and as illustrated for example in FIG. 8b, a tightly wound coil electrode 74b may be substantially flat, rectangular in cross-section.

A flat cross-section is preferred for a number of reasons. With a flat cross section, the tissue contact surface area of the coil electrode 74b can be increased along the support structure 72, as compared to the coil electrode 74a with a circular cross-section, without increasing the outside diameter of the electrode. This results in more compact and easily deployable electrodes. A flat cross-section also permits a more efficient transmission of radio frequency energy. With a flat cross-section, the radio frequency electrical energy is transmitted through a rectangular cross-sectional area that is many times that of the cross-section of a round wire of identical thickness. Also, substantially fewer windings are required to construct a coil electrode with a flat cross-section. As a result, there is a lower electrical impedance for a flat cross-section wire.

Whether circular or rectangular in cross-section, the flexibility of coil electrodes can be increased by introducing space between the coil windings. As illustrated for example in FIGS. 9a and 9b, the windings in each of the coil electrodes 76a and 76b have been spread apart by a distance D, which is the result of increasing the pitch of the individual windings. Here too, the cross-section of the coil electrodes can be either circular (electrode 76a) or rectangular (electrode 76b). Preferably, the distance D between the windings should be at least ⅕ of the width W of the windings. The most preferred distance D is believed to be about ½ of the width W of the windings. However, the actual spacing will depend upon the desired heating effect. If additive heating effects between adjacent windings are desired to form continuous lesions between the windings, the upper spacing limit becomes the distance at which the desired additive heating effect is observed to diminish.

Temperature sensors, such as thermocouples or thermistors, are provided in conjunction with electrodes in many electrophysiological probes. As illustrated for example in FIGS. 10 and 11, the longitudinal ends of a coil electrode 78 may be configured to accommodate optimal placement of temperature sensors 80. The coil electrode 78 includes a first zone 82 with spaced windings, which represents the majority of the electrode, and second zones 84 at each longitudinal end of the electrode with closely adjacent windings. In the illustrated embodiment, the spacing D between adjacent windings in the first zone 82 is substantially uniform. However, the spacing D can also be varied by, for example, progressively decreasing the spacing from the midpoint of the first zone 82 to the second zones 84. Whether uniform or varied, the spacing D should be at least ⅕ of the width W. The closeness of the. windings in the second zones 84 provides a support structure for the temperature sensors 80 which are preferably mounted at or near the longitudinal end edges of the coil electrodes 78. It is at the edges where electrical conductivity is discontinuous and the resulting rise in current density generates localized regions of increased power density and, therefore, higher temperatures.

The temperature sensors may be mounted in a variety of ways. For example, as shown in solid lines in FIG. 11, the temperature sensors 80 may be threaded up through the windings in the second zones 84 to lay upon their exterior surfaces and encapsulated in an epoxy or cyanoacrylate adhesive or PTFE coating 86. Preferably, as shown in phantom lines in FIG. 11, the temperature sensors 80 can be secured to the inside surface of each of the second zones 84. The sensors 80 may also be sandwiched between the inside surface of the second zones 84 and the support structure 72. A thin strip of electrically insulating material (not shown) may be applied about the support structure 72 immediately next to the second zones 84 to help to minimize the presence of edge effect currents.

In accordance with a present invention, the coil electrodes disclosed herein preferably have a relatively high level of resiliency as well as a relatively high level of radiopacity. In the preferred embodiment, and as shown by way of example in FIG. 12, the coil electrode 78 (the construction of which may also be applicable to the other electrodes disclosed herein) is a composite coil electrode formed from a first material 88 having a relatively high radiopacity and a second material 90 having a relatively high resiliency. The first material 88 may, for example, be relatively soft and significantly less stiff than the second material 90. Although the preferred configuration is one in which the first material 88 having the relatively high radiopacity is generally interior to the second material 90 having the relatively high resiliency, the relative positioning of the materials may be reversed.

The first and second materials may be combined in a drawn filled tubing arrangement that is subsequently rolled into a flat wire, or through other techniques. For example, the first and second materials may be combined into a multifilament drawn wire including individual strands of the first and second materials. Such a wire may be obtained from Cathguide Corp. in Miami, Fla. Another method of combining the first and second materials involves placing a heat expanded hypotube formed from the second material over a hypotube formed from the first material. Cooling of the second material will cause the hypotube formed therefrom to shrink fit over the hypotube formed from the first material, thereby forming a composite hypotube that can be drawn to size using conventional techniques.

One exemplary method of manufacturing the coil electrode 78 is to wind drawn, filled tubing or multifilament wire having the desired combination of metals around a mandrel in accordance with conventional coil fabrication techniques. In those instances where the coil electrode 78 is configured in the manner illustrated in FIG. 10, the windings in the second zones 84 are connected to one another to prevent unraveling (preferably by laser welding) and the longitudinal ends are cut and ground to a 90 degree angle with the longitudinal axis of the coil. Alternatively, the drawn, filled tubing can be wound directly onto the support structure 72. Another manufacturing method involves machining the aforementioned composite hypotube, or a hypotube made of one material (such as stainless steel) into a series of spiral coils, thereby forming the coil electrode. Suitable machining techniques include laser cutting, chemical etching and electrical discharge machining. When the hypotube is only made of one material, the machined coil electrode can then be coated with another material (such as gold) by techniques including electroplating, conductive adhesives and ion vapor assisted deposition.

In any of these configurations, the result of this composite construction is a durable coil electrode that has the resiliency necessary for winding and/or assembly processes, the flexibility necessary for imparting resiliency to the distal portion of the probe, as well as the radiopacity necessary for fluoroscopic imaging.

In the exemplary embodiment illustrated in FIG. 12, the coil electrode 78 includes a stainless steel cladding (second material 90) over a 90/10 platinum/iridium core (first material 88). Alternate first materials 88 include platinum, gold, silver, tantalum and other radiopaque precious metals. The stainless steel is preferably 304, 303, or 17-7. Alternate second materials 90 include Nitinol and titanium. Preferably, the percent recoverable strain of the second material 90 will be at least 2% to provide sufficient resiliency.

Preferably, the radiopacity of the first material 88 will be at least two (2) times the radiopacity of the second material 90. By way of background, medical fluoroscopy utilizes a low energy x-ray system wherein photoelectric absorption, as opposed to Compton scattering or other ways in which x-rays interact with matter, becomes the predominant factor. As a result, in most surgical and interventional procedures, the degree of visibility will be dependent on the atomic weight of the material. Stainless steel, for example, has an atomic weight 57.50, while 24 K gold and 90/10 platinum/iridium have respective atomic weights of 196.97 and 194.80. Thus, the radiopacity of 24K gold and 90/10 platinum/iridium is about 3.4 times that of stainless steel.

With respect to dimensions, the coil electrodes 78 may be sized to suit particular applications. For example, a coil electrode for use in a catheter-type electrophysiological probe is preferably between about 6 mm and 18 mm in length and between about 1.6 mm and 3 mm in outer diameter, while the coil electrodes in surgical probe will preferably be between about 6 mm and 18 mm in length and between about 1.6 mm and 3 mm in outer diameter. The thickness of the electrodes will be preferably between about 0.003 inch and 0.012 inch, with the thickness of the first material 88 having a relatively high radiopacity being between about 0.001 inch and 0.005 inch and the thickness of the second material 90 having a relatively high resiliency being between about 0.002 inch and 0.008 inch. The thickness ratio of the first material 88 to the second material 90 is preferably between about 0.3 and 3.

Turning to electrode spacing, the spacing between the electrodes is equal to or less than about 3 times the smaller of the diameters of the electrodes, the simultaneous emission of energy by the electrodes creates an elongated continuous lesion pattern in the contacted tissue area due to the additive effects. Similar effects are obtained when the spacing between the electrodes is equal to or less than about 2 times the longest of the lengths of the electrodes.

To consistently form long, continuous curvilinear lesion patterns, additional spatial relationships among the electrodes must be observed. When the length of each electrode is equal to or less than about 5 times the diameter of the respective electrode, the curvilinear path that the probe takes should create a distance across the contacted tissue area that is greater than about 8 times the smaller of the diameters of the electrodes. The simultaneous application of energy will form a continuous elongate lesion pattern that follows the curved periphery contacted by the probe, but does not span across the contacted tissue area. The same effect will be obtained when the length of each electrode is greater than about 5 times the diameter of the respective electrode, and the curvilinear path that support element takes should create a radius of curvature that is greater than about 4 times the smallest the electrode diameters. Of course, the spacing between the electrodes must be such that additive heating effects are created.

Taking the above considerations into account, the consistent formation of continuous lesions can be obtained, when using coil electrodes that are about 12.5 mm in length and about 2.33 mm in diameter, with about 2 to 3 mm electrode spacing.

As the aforementioned sizes and spacings facilitate the production a variety of lesions, including large surface area, deep lesions and continuous long thin lesions, the present probes are especially useful in treating atrial flutter, atrial fibrillation, other supraventricular tachycardias, and ventricular tachycardia substrates. These electrode configuration also provides detailed mapping capabilities.

IV. Electrode Identification

Figure 13:
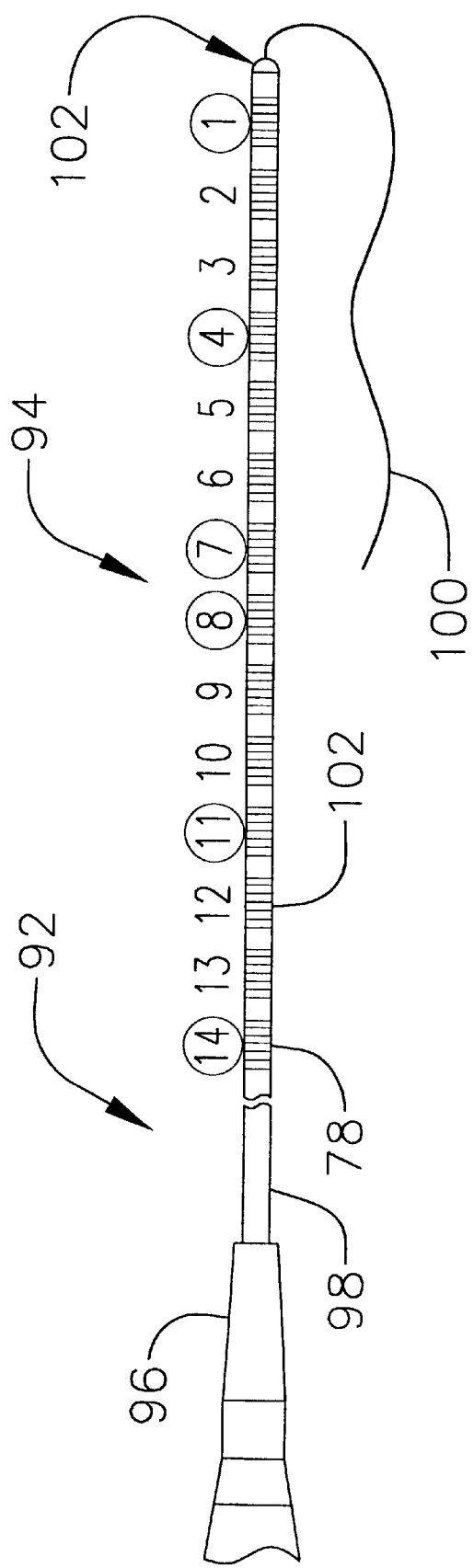
FIG. 13 is a partial plan view of an electrophysiological probe in accordance with a preferred embodiment of a present invention.

As illustrated for example in FIG. 13, an electrophysiological probe 92 in accordance with a preferred embodiment of a present invention includes an electrode array 94 that facilitates individual electrode identification when the probe is viewed with a fluoroscope. Although the exemplary array, as well as variations thereof, can be used in combination with a wide variety of electrophysiological probes, exemplary probe 92 is a loop catheter having a handle 96, a catheter body including a distal portion 98, a pull wire 100, and a radiopaque distal marker 102. Additional information concerning loop catheters may be found in U.S. Pat. No. 5,910,129, which is incorporated herein by reference.

The exemplary array 94 includes a plurality of radiopaque coil electrodes 78 (described in Section III above with reference to FIGS. 10–12) and a plurality of electrodes 104 that have lower radiopacity. Here, the electrodes 104 are stainless steel coil electrodes. The exemplary array 94 includes fourteen (14) electrodes numbered 1–14 with the radiopaque coil electrodes 78 identified with circles around their respective electrode numbers in FIG. 13. The array 94 is divided into two sets-the distal set (electrodes 1–7) and the proximal set (electrodes 8–14). The proximal-most and distal-most electrodes in each set (electrodes 1,7, 8 and 14) are radiopaque coil electrodes 78. Stainless steel electrodes 104 (electrodes 2,6, 9 and 13) are located proximal to the distal-most electrode and distal to the proximal-most electrode in each set. This arrangement facilitates identification of the distal-most electrode (electrode 1) and the proximal-most electrode (electrode 14). The center point of the overall array is also easily identifiable in that it is the only portion of the array that has two consecutive radiopaque electrodes 78. In order to provide additional resolution, radiopaque electrodes 78 (electrodes 4 and 11) may also be placed at the mid-points of each set.

Accordingly, and although other patterns may be used, the juxtaposition of the more radiopaque coil electrodes 78 with the stainless steel coil electrodes 104 in a predetermined pattern allows the physician to easily distinguish between the various electrodes in the array.

For certain surgical probe applications, such as surgical probes that can be used during open heart surgery in addition to less invasive procedures, the coils may be color coded for positive visual identification by the physician. A number of different colors (including the color of metal that is not otherwise colored) may be employed in the coding schemes and various conventional techniques may be used to apply a colored coating. For example, a thin layer of gold may be deposited onto the exterior surface of the electrode by ion vapor deposition. Titanium plating, which can be processed into a blue color, can also be used. Another technique involves the use of platinum black which, as is known in the medical arts, is platinum that is made to look black through the use of surface modification techniques.

The arrangement (or pattern) of the color coded electrodes may, if desired, correspond to the coding arrangement illustrated in FIG. 13. Color coding may also be used in combination with radiopacity-based coding by, for example, making the more radiopaque electrodes one color and the less radiopaque electrodes another color so that the electrodes can be identified both visually and through fluoroscopy.

Although the present inventions have been described in terms of the preferred embodiments above, numerous modifications and/or additions to the above-described preferred embodiments would be readily apparent to one skilled in the art. It is intended that the scope of the present inventions extends to all such modifications and/or additions.

We claim:

1. An electrophysiology probe, comprising:
   a support structure; and
   at least one coil electrode supported on the support structure, the at least one coil electrode being formed from a first material defining an outer surface and having a relatively high radiopacity and a second material having a relatively high resiliency, at least a portion of the second material being located radially outwardly of the outer surface of the first material.

2. An electrophysiology probe as claimed in claim 1, wherein the first material comprises platinum.

3. An electrophysiology probe as claimed in claim 1, wherein the second material comprises stainless steel.

4. An electrophysiology probe as claimed in claim 1, wherein the first material defines a radiopacity substantially equal to at least approximately 2 times the radiopacity of the second material.

5. An electrophysiology probe as claimed in claim 1, wherein the second material defines a percent recoverable strain substantially equal to at least approximately 2%.

6. An electrophysiology probe as claimed in claim 1, wherein the first material defines a core and the second material defines a cladding over the core.

7. An electrophysiology probe as claimed in claim 1, further comprising:

an electrical lead wire connected to the at least one electrode.

8. An electrophysiology probe as claimed in claim 1, wherein the support structure comprises a catheter body.

9. An electrophysiology probe as claimed in claim 1, wherein the support structure comprises a relatively short shaft.

10. An electrophysiology probe, comprising:

a support structure; and an energy transmission device including a first tubular member having a relatively high radiopacity and a second tubular member secured to the first tubular member and having a relatively high resiliency.

11. An electrophysiology probe as claimed in claim 10, wherein the support structure comprises a catheter body.

12. An electrophysiology probe as claimed in claim 10, wherein the support structure comprises a relatively short shaft.

13. An electrophysiology probe as claimed in claim 10, wherein the first and second tubular members comprise first and second hypotubes.

14. An electrophysiology probe as claimed in claim 10, further comprising:

a spiral groove extending through the first and second tubular members and longitudinally along at least a portion of the energy transmission device.

15. An electrophysiology probe as claimed in claim 10, wherein the first tubular member comprises a platinum tubular member.

16. An electrophysiology probe as claimed in claim 10, wherein the second tubular member comprises a stainless steel tubular member.

17. An electrophysiology probe as claimed in claim 10, wherein the first tubular member defines a radiopacity substantially equal to at least approximately 2 times the radiopacity of the second tubular member.

18. An electrophysiology probe as claimed in claim 10, wherein the second tubular member defines a percent recoverable strain substantially equal to at least approximately 2%.

19. An electrophysiology probe as claimed in claim 10, wherein the second tubular member is positioned over the first tubular member.

20. An electrophysiology probe as claimed in claim 10, wherein the first tubular member is positioned over the second tubular member.

21. An electrophysiology probe as claimed in claim 10, further comprising:

an electrical lead wire connected to the at least one energy transmission device.

* * * * *